United States Patent
Palanker et al.

(10) Patent No.: US 8,105,324 B2
(45) Date of Patent: Jan. 31, 2012

(54) METHODS AND DEVICES FOR THE NON-THERMAL, ELECTRICALLY-INDUCED CLOSURE OF BLOOD VESSELS

(75) Inventors: Daniel V. Palanker, Sunnyvale, CA (US); Alexander B. Vankov, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1083 days.

(21) Appl. No.: 11/663,672

(22) PCT Filed: Sep. 20, 2005

(86) PCT No.: PCT/US2005/033856
§ 371 (c)(1),
(2), (4) Date: Nov. 1, 2007

(87) PCT Pub. No.: WO2006/036706
PCT Pub. Date: Apr. 6, 2006

(65) Prior Publication Data
US 2008/0188846 A1  Aug. 7, 2008

Related U.S. Application Data

(60) Provisional application No. 60/612,835, filed on Sep. 24, 2004.

(51) Int. Cl.
*A61B 18/00* (2006.01)
(52) U.S. Cl. ........................................... 606/41
(58) Field of Classification Search .................. 606/41
See application file for complete search history.

(56) References Cited

U.S. PATENT DOCUMENTS

| 3,885,569 | A | * | 5/1975 | Judson ........................ 606/37 |
| 5,088,977 | A | | 2/1992 | Sibalis |
| 5,403,311 | A | * | 4/1995 | Abele et al. ................ 606/49 |
| 5,704,908 | A | * | 1/1998 | Hofmann et al. .......... 604/21 |
| 6,050,952 | A | * | 4/2000 | Hakki et al. ............... 600/485 |
| 6,192,270 | B1 | * | 2/2001 | Hofmann et al. .......... 604/20 |
| 6,228,082 | B1 | | 5/2001 | Baker et al. |

(Continued)

FOREIGN PATENT DOCUMENTS

WO   WO-00/32127 A1   6/2000

(Continued)

OTHER PUBLICATIONS

Gregor Sersa et al. (Q1 2003) "Tumor blood flow modifying effects of electrochemotherapy: a potential vascular targeted mechanism", Radiol Oncol, 37(1):43-8.*

(Continued)

*Primary Examiner* — Michael Peffley
*Assistant Examiner* — Daniel Fowler
(74) *Attorney, Agent, or Firm* — Morrison & Foerster LLP

(57) ABSTRACT

Methods and devices for the non-thermal, electrically-induced temporary or permanent closure of blood vessels. The subject methods and devices employ pulsed electrical energy according to a defined regime to effect controlled occlusion of targeted blood vessels without heating the vessel and with minimal damage to adjacent tissue. The extent of vessel closure, i.e., temporary (vasoconstriction) or permanent (thrombosis), is controlled based on the manipulation of various parameters of the electrical stimulation regime as well as the configuration of the electrodes used to apply the regime.

20 Claims, 6 Drawing Sheets

U.S. PATENT DOCUMENTS

| | | | |
|---|---|---|---|
| 6,274,558 | B1 | 8/2001 | Haupert, Jr. |
| 6,461,354 | B1 | 10/2002 | Olsen et al. |
| 6,520,950 | B1 * | 2/2003 | Hofmann et al. ............. 604/503 |
| 6,623,454 | B1 | 9/2003 | Eggers et al. |
| 6,685,812 | B2 | 2/2004 | Miles |
| 2003/0023285 | A1 | 1/2003 | Eggers et al. |
| 2003/0097126 | A1 | 5/2003 | Woloszko et al. |
| 2003/0134811 | A1 | 7/2003 | Jackson et al. |
| 2004/0054366 | A1 | 3/2004 | Davison et al. |
| 2004/0162554 | A1 | 8/2004 | Lee et al. |
| 2004/0186470 | A1 | 9/2004 | Globe et al. |

FOREIGN PATENT DOCUMENTS

| | | |
|---|---|---|
| WO | WO-01/93950 A1 | 12/2001 |
| WO | WO-03/103522 A1 | 12/2003 |

OTHER PUBLICATIONS

New Zealand Examination Report mailed on Apr. 23, 2009, for New Zealand Patent Application No. 553915, filed on Sep. 20, 2005, two pages.

European Search Opinion mailed on Nov. 4, 2010, for EP Application No. 05798867.7, filed on Sep. 20, 2005, four pages.

Supplemental European Search Report mailed on Nov. 4, 2010, for EP Application No. 05798867.7, filed Sep. 20, 2005, three pages.

Braunschweiger, P.G. et al. (Nov. 1, 1988). "Antitumor Effects of Recombinant Human Interleukin 1α in RIF-1 and Panc02 Solid Tumors," *Cancer Research* 48:6011-6016.

Brown, J.M. (Jul. 1987). "Exploitation of Bioreductive Agents with Vasoactive Drugs" In *Proceedings of the 8th International Congress on Radiation Research*, Fielden, E.M. et al. eds., Taylor and Francis: London, 2:719-724.

Chaplin, D.J. et al. (Apr. 1987). "The Effect of Hydralazine on the Tumor Cytotoxicity of the Hypoxic Cell Cytotoxin RSU-1069: Evidence for Therapeutic Gain," *International Journal of Radiation Oncology Biology Physics* 13(4):579-585.

Chaplin, D.J. (1991). "The Effect of Therapy on Tumour Vascular Function," *International Journal of Radiation Biology* 60(1/2):311-325.

Denekamp, J. et al. (Feb. 1983). "Vascular Occlusion and Tumour Cell Death," *European Journal of Cancer & Clinical Oncology* 19(2):271-275.

Fingar, V.H. et al. (Nov. 1987). "Drug and Light Dose Dependence of Photodynamic Therapy: A Study of Tumor and Normal Tissue Response," *Photochemistry and Photobiology* 46(5):837-841.

Gamarra, F. et al. (Apr. 1, 1993). "High-Energy Shock Waves Induce Blood Flow Reduction in Tumors," *Cancer Research* 53:1590-1595.

Guarini, S. (Apr. 1996). "A Highly Reproducible Model of Arterial Thrombosis in Rats," *Journal of Pharmacological and Toxicological Methods* 35(2):101-105.

Hill, S.A. et al. (Sep. 27, 1995). "Anti-Vascular Approaches to Solid Tumor Therapy: Evaluation of Vinblastine and Flavone Acetic Acid," *International Journal of Cancer* 63(1):119-123.

International Search Report mailed on Feb. 21, 2006, for PCT Application No. PCT/US05/33856 filed on Sep. 20, 2005, four pages.

Kallinowski, F. et al. (Oct. 1989). "In Vivo Targets of Recombinant Human Tumour Necrosis Factor-α: Blood Flow, Oxygen Consumption and Growth of Isotransplanted Rat Tumours," *British Journal of Cancer* 60(4):555-560.

Naredi, P.L.J. et al. (Jun. 19, 1993). "The Effects of Tumour Necrosis Factor Alpha on the Vascular Bed and Blood Flow in an Experimental Rat Hepatoma," *International Journal of Cancer* 54(4):645-649.

Nilsson, F. et al. (Jan. 15, 2001). "Targeted Delivery of Tissue Factor to the ED-B Domain of Fibronectin, a Marker of Angiogenesis, Mediates the Infarction of Solid Tumors in Mice," *Cancer Research* 61:711-716.

Peterson, H-I. (1979). *Tumor Blood Circulation: Angiogenesis, Vascular Morphology and Blood Flow of Experimental and Human Tumors*, CRC Press, Inc.: Baca Raton, FL, 2 pages.

Ran, S. et al. (Oct. 15, 1998). "Infarction of Solid Hodgkin's Tumors in Mice by Antibody-directed Targeting of Tissue Factor to Tumor Vasculature," *Cancer Research* 58:4646-4653.

Serša, G. et al. (Apr. 1999). "Tumour Blood Flow Changes Induced by Application of Electric Pulses," *The European Journal of Cancer* 35(4):672-677.

Song, C.W. (Oct. 1984). "Effect of Local Hyperthermia on Blood Flow and Microenvironment: A Review," *Cancer Research* (Suppl.) 44:4721s-4730s.

Stratford, I.J. et al. (Aug. 1988). "Potentiation of the Anti-Tumour Effect of Melphalan by the Vasoactive Agent, Hydralazine," *British Journal of Cancer* 58(2):122-127.

* cited by examiner

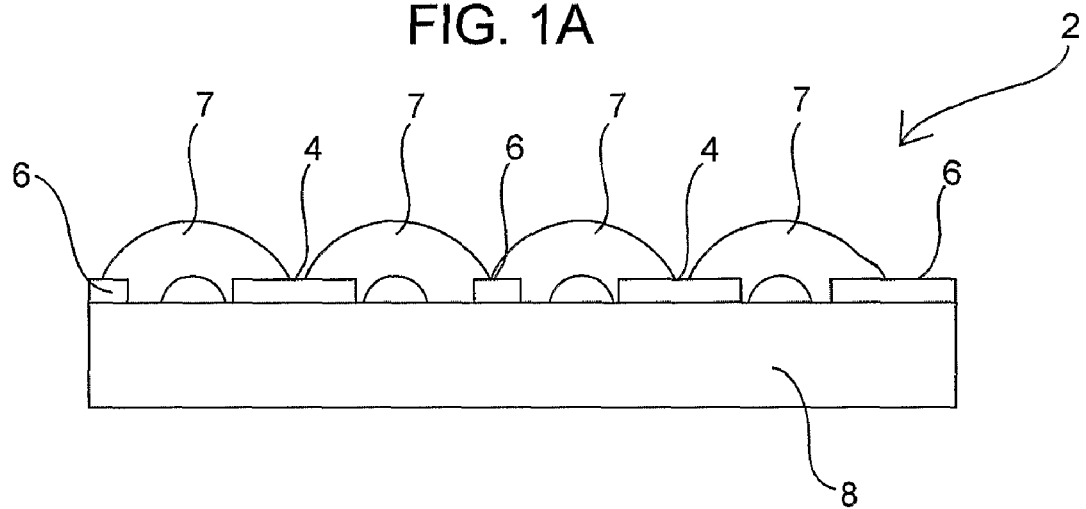
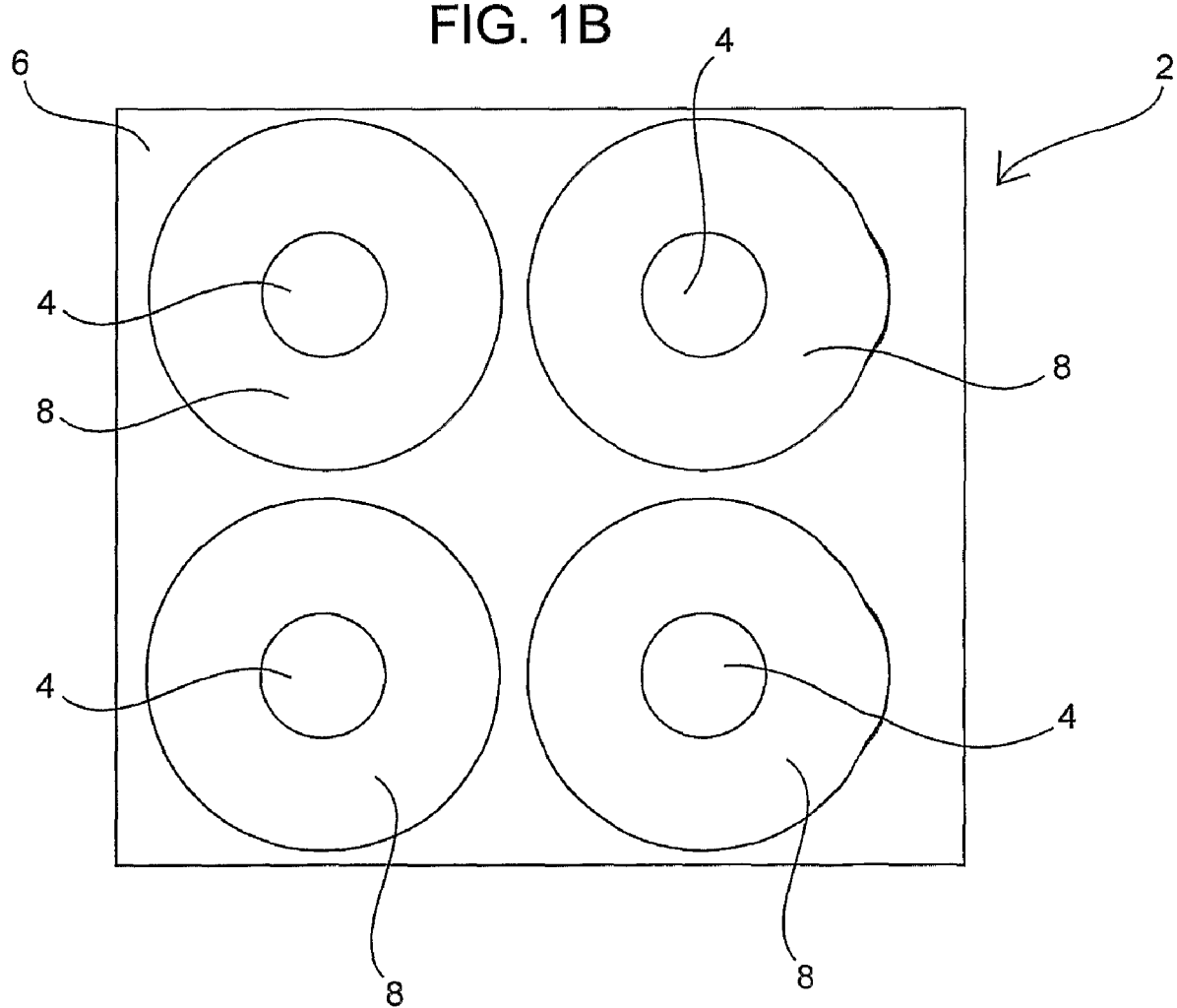

METHODS AND DEVICES FOR THE NON-THERMAL, ELECTRICALLY-INDUCED CLOSURE OF BLOOD VESSELS

FEDERALLY-SPONSORED RESEARCH OR DEVELOPMENT

This invention was made with Government support under contract EY012888awarded by the National Institutes of Health. The Government has certain rights in this invention.

CROSS-REFERENCE TO RELATED APPLICATIONS

This application is a National Phase filing under 35 U.S.C. §371 of International Application No. PCT/US2005/033856 filed Sept. 20, 2005, which claims priority to U.S. Provisional Patent Application No. 60/612,835 filed Sep. 24, 2004, the contents of which are incorporated herein by reference in their entirety.

BACKGROUND OF THE INVENTION

An objective of a variety of medical applications is to selectively compromise or destroy vascular function. One such application is the treatment of solid tumors. It has been shown that a reduction in tumor blood flow reduces nutrients to the tumor and causes accumulation of catabolite products and extracellular acidification, all of which result in a cascade of tumor cell death. Brown, J. M., Exploitation of bioreductive agents with vasoactive drugs, In Fiedlen E. M., Fowler J. F., Hendry J. H., Scott D., eds. Proceedings of the Eight International Congress on Radiation Research, Edinburg UK, Vol. 2, London, Taylor and Francis, 1987, 719-724; Chaplin D J, Acker B., The effect of hydralazine on the tumor cytotoxicity of the hypoxic cell cytotoxin RSU-1069: evidence for therapeutic gain; Int J Radiant Oncol Biol Phys 1987, 13, 579-585; Stratford I. J., Adams G. E., Godden J., Nolan J., Howells N., Timpson N.; Potentiation of the anti-tumor effect of melphalan by the vasoactive agent, hydralazine. Br. J. Cancer 1988, 58, 122-127; Denekamp J, Hill S A, Hobson B, Vascular occlusion and tumor cell death, Eur. J. Cancer Clin. Oncol. 1983, 19, 271-275.

One approach to creating vascular dysfunction involves inducing tumor-selective thrombosis that shuts down the blood supply to the tumor cells (S. Ran, B. Gao, S. Duffy, L. Watkins, N. Rote, P. E. Thorpe, Cancer Res. 58 (1998) 4646-3653; F. Nilsson, H. Kosmehl, L. Zardi, D. Neri, Cancer Res. 61 (2001) 711-716). There are many anticancer drugs and agents which have been shown to cause such thrombosis, including cytokines (P. L. J. Naredi, P. G. Lindner, S. B. Holmberg, U. Stenram, A. Peterson and L. R. Hafstrom, The effects of tumour necrosis factor alpha on the vascular bed and blood flow in an experimental rat hepatoma, Int. J. Cancer 54 (1993), pp. 645-649; F. Kallinowski, C. Schaefer, G. Tyler and P. Vaupel, In vivo targets of recombinant human tumor necrosis factor-a: blood flow, oxygen consumption and growth of isotransplanted rat tumours; Br. J. Cancer 60 (1989), pp. 555-560; P. G. Braunschweiger, C. S. Johnson, N. Kumar, V. Ord and P. Furmonski, Antitumor effects of recombinant human interleukin 1α in RIF-1 and PancO2 solid tumors, Cancer Res. 48 (1988), pp. 6011, 6016), serotonin, flavone acetic acid (D. J. Chaplin, The effect of therapy on tumor vascular function; Int. J. Radiat. Biol. 60 (1991), pp. 311, 325) and vinca alkaloids (S. A. Hill, L. E. Sampson and D. J. Chaplin, Anti-vascular approaches to solid tumor therapy: evaluation of vinblastine and flavone acetic acid; Int. J. Cancer 63 (1995), pp. 119-123). However, the effectiveness of many of these agents is limited by the risk of unacceptable system toxicity (G. Sersa, M. Cemasar, C. S. Parkins and D. J. Chaplin: Tumor blood flow changes induced by application of electric pulses, European Journal of Cancer 35, N. 4, (1999) pp. 672-677), among other factors.

Various other types of therapies have also been shown to affect some degree of vascular dysfunction in tumors, including hyperthermia (C. W. Song, Effect of local hyperthermia on blood flow and microenvironment, Cancer Res. 44 (1984), pp. 4721-4730), photodynamic therapy (V. H. Fingar and B. W. Henderson, Drug and light dose dependence of photodynamic therapy: a study of tumour and normal tissue response. Photochem. Photobiol. 46 (1987), pp. 837-841) and high-energy shock wave therapy (F. Gamarra, F. Spelsberg, G. E. H. Kuhnle and A. E. Goetz, High-energy shock waves induce blood flow reduction in tumors, Cancer Res. 53 (1993), pp. 1590-1595). However, complete and permanent hemostasis has not yet been achieved by these methodologies. Mechanical clamping of the tumor-supporting vasculature has also been proposed (Denekamp J, Hill S. A., Hobson B., Vascular occlusion and tumor cell death, Eur. J. Cancer Clin. Oncol. 1983, 19, 271-275), however, such technique may be impractical due to the extremely twisted and branched nature of tumor vasculature.

Another application involving the selective destruction of vascular function is in the treatment of cutaneous vascular disorders, such as telangiectasia (commonly known as "spider veins") and in the removal of cutaneous vascular lesions, e.g., capillary hemangiomas (such as cafe-au-lait spots and port wine stains). These conditions all involve dilated or engorged capillaries in the skin. While not often of physical concern, they can be unsightly and cause emotional distress to the patient.

The most common treatment used for cutaneous vascular lesions is sclerotherapy, which entails the intravascular injection of one of a variety of agents into the abnormal blood vessels. The injected substance injures the interior walls of the capillary causing it to shrink or disappear. Unfortunately, this treatment can be painful, only partially effective, and usually requires about one to two months before improvement can be seen. In addition, undesirable side effects can occur, such as echymotic or hyperpigmented marks, which may take months to completely fade away.

Other treatments such as freezing, surgery, radiation, phototherapy and laser therapy have also been employed for subcutaneous and cutaneous vascular conditions. Of these, the use of lasers has been the most successful as the destruction of the offending capillaries is achieved with the least amount of damage to the overlying skin. However, laser therapy is not without its shortcomings. The blood hemoglobin absorbs the laser light and the resulting hyperthermia leads to coagulation of the blood within the vessels in the surface layer of the skin. Where the affected skin area is relatively deep, the more superficial capillaries absorb the majority of the light energy and the remaining energy is insufficient to effectively treat the deeper vessels (referred to as "shadowing"). This problem can be solved to some degree by use of less absorbent wavelengths, however, this is at the sake of a reduced ability to localize heat, which may necessitate longer treatments and/or multiple treatments which are both expensive and time-consuming. Additionally, laser therapy does not work as well with patients having a darker skin pigment as the epidermal melanin absorbs a significant portion of the light to which it is exposed, thus, reducing the amount of light that is able to reach the blood. The increase in the intensity of the laser required to compensate for interference from tissue and melanin may lead to thermal injury of the skin and to post-inflammatory pigment changes.

Many recent improvements in electrosurgical technology, particularly in bipolar electrosurgical devices, have made it easy to use in surgical and other therapeutic settings. Ostensibly, electrosurgery may be a viable alternative to the above-described modalities for treating tumors and cutaneous and subcutaneous vascular disorders. However, current electrosurgical devices and procedures are based on the thermal denaturation and coagulation of tissues and still suffer from significant thermal damage to surrounding tissue, and an inability to accurately control the depth of necrosis in the tissue being treated. Additionally, the application of current to tissue results in electrochemical reactions which lead to the accumulation of toxic products on the electrodes that may cause cytolysis of the surrounding tissue (Peterson H. I., Tumor Blood Circulation Angiogenesis, Vascular Morphology and Blood Flow of Experimental and human tumors, Florida, CRC Press, 1979, 1-229). In addition, hydrolysis on the electrodes emits gases which may interfere with current transmission, making the treatment unpredictable and unstable (S. Guarini, A Highly Reproducible Model of Arterial Thrombosis in Rats, *Journal of Pharmacological and Toxicological Methods*, 35 (1996) pp 101-105). These shortcomings are particularly significant in applications in which the target area is extremely small, e.g., capillary vessels having diameters in the range from about 10 to about 100 μm.

Accordingly, there is still a need for improved methodologies for creating hemostasis within blood vessels without causing damage to adjacent tissue. In particular, there is a need for a more effective and safe way to treat solid tumors and cutaneous and subcutaneous vascular disorders.

SUMMARY OF THE INVENTION

The present invention provides methods and devices for the non-thermal, electrically induced temporary or permanent closure of blood vessels. The subject methods and devices employ short pulses of electrical current according to a defined regime to effect a controlled occlusion of targeted blood vessels without heating the vessel and with minimal electrochemical damage to adjacent tissue. The extent of vessel closure, i.e., temporary (vasoconstriction) or permanent (occlusion), is controlled based on the manipulation of various parameters of the electrical stimulation regime as well as the configuration of the electrodes used to apply the regime.

The subject methods include the application of short-duration electrical pulses to induce an electrical field to the targeted blood vessel(s) and thereby cause the occlusion of the blood vessel(s). The treatment regimes employed in the subject methods may be optimized for a particular application by the selection of various parameters of the treatment regime. These parameters include but are not limited to pulse duration, the polarity of the pulses, pulse frequency, the frequency of the pulses within a burst, the duration of a burst, the duration of the treatment regime, and the number of sets of bursts within a treatment regime.

The subject devices include an electrode configuration having a geometry selected specifically for application to target tissue region, where the depth and surface area of the affected tissue region are considerations dictating an optimal electrode configuration. In one variation, an array of active electrodes is provided with a larger return electrode situated remotely from the active electrodes. In another variation, each active electrode is provided with a surrounding return electrode.

One object of the invention is to selectively induce hemostasis within blood vessels by creating thrombosis within the vessels with minimal side effects, fewer steps and less discomfort to the patient than has heretofore been possible.

The present invention is useful in treating solid tumors, aneurysms, vascular malformations, arteriovenous fistulas (e.g., carotid-cavernous, vertebral), internal arterial bleeding sites, damaged vessels following-trauma and the like, and cutaneous and subcutaneous vascular conditions, such as port wine stains.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIGS. 1A and 1B illustrate cross-sectional and top views, respectively, of an embodiment of an electrode configuration suitable for use with the present invention.

DETAILED DESCRIPTION OF THE INVENTION

Figure 2A:
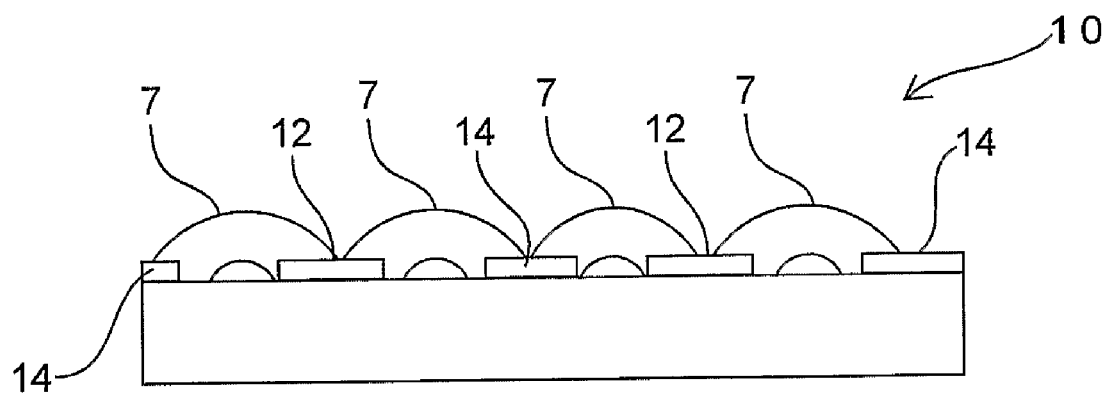
FIGS. 2A and 2B illustrate cross-sectional and top views, respectively, of another embodiment of an electrode configuration suitable for use with the present invention.

Before the subject devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a pulse" includes a plurality of such pulses and reference to "the electrode" includes reference to one or more electrodes and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Generally, the methods of the present invention include the application of an electrical current stimulation regime having a pulsatile waveform to a target tissue area or one or more targeted blood vessels and which produces an electric field in the targeted area sufficient to cause occlusion of the target vessels.

The pulsatile waveform includes current pulses of monophasic or bi-phasic (alternating) polarities that produce the desired occlusion in the target vessel(s) while maintaining the target tissue at acceptable temperatures, i.e., below the temperature at which irreversible tissue destruction occurs. Accordingly, the average temperature rise in the treated tissue area during the electrical stimulation procedure is no more than about 10° C. The pulsed electrical treatment with bi-phasic pulses according to the subject methods also avoids irreversible electrochemical reactions on the electrodes, thereby reducing tissue damage.

In certain variations, the treatment regime includes the application of one or more pulses or bursts of pulses. Typically, the regime involves at least two pulses or bursts, and more typically, it applies a plurality of pulses or bursts in a periodic fashion for several minutes where permanent or irreversible occlusion of the target blood vessel(s) is desired.

The necessary scope or depth of the electric field to be applied to the target area depends at least in part on the depth of the targeted blood vessels from the tissue or skin surface against which the electrodes are contacted. Where only shallow penetration of the electric field is required over a relatively large surface area, for example when treating cutaneous vascular disorders, a preferable electrode configuration or geometry includes either a sequentially-activated array of small active electrodes with a larger remotely-positioned return electrode, or an array of active electrodes each of which is surrounded by the closely-spaced return electrodes (bipolar geometry). In the second variation, the electrodes in the array may be activated simultaneously.

Figure 2B:
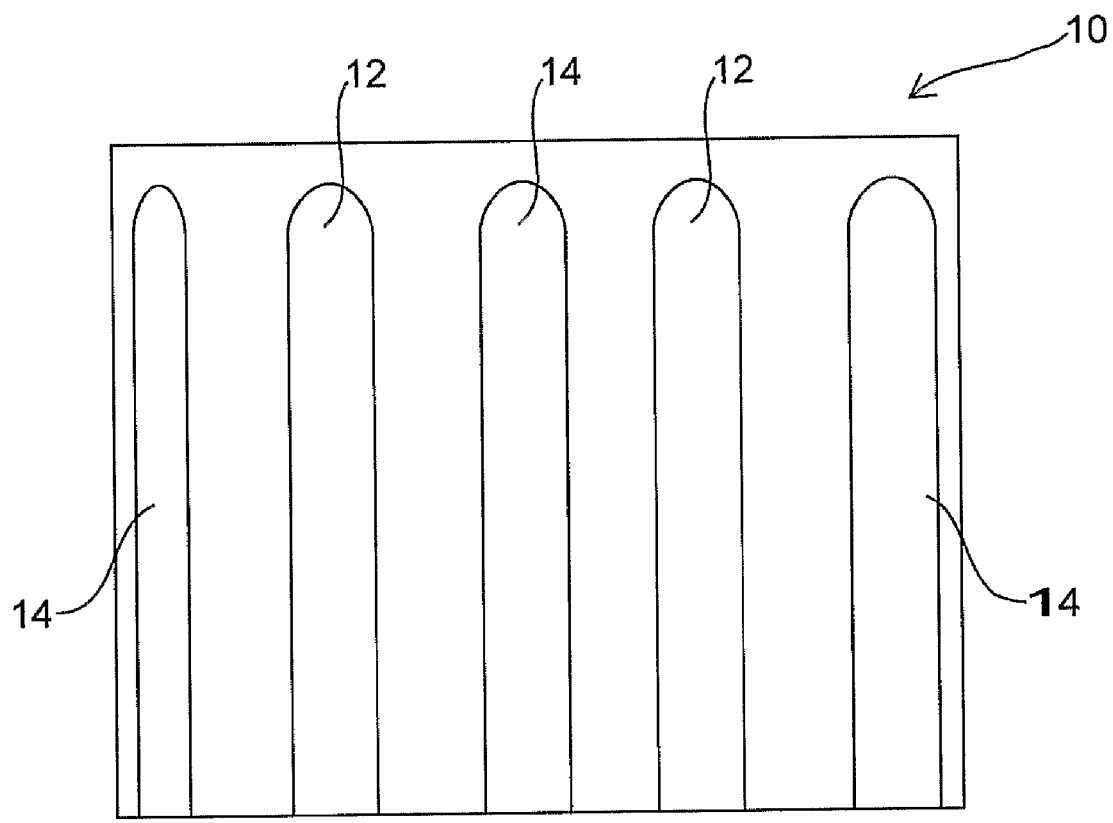

An example of such an electrode configuration suitable for use with the present invention is illustrated in FIGS. 1A and 1B. Electrode assembly 2 includes a planar (two-dimensional) array of active electrodes 4 distributed over a distal contact surface of a probe (not shown) mounted on an insulating substrate or support material 8, such as silicone elastomer. Active electrodes 4 are in the form of isolated dots or points concentrically surrounded by but spaced from a single, larger return electrode 6 extending over substrate 8. Another electrode configuration suitable for use with the present invention is illustrated in FIGS. 2A and 2B. Here, electrode assembly 10 includes an array of parallel lines or strips of active electrodes 12 and return electrodes 14 mounted on where the active and return electrodes are interspaced with each other in an alternating fashion.

With a bipolar configuration (FIGS. 1 and 2), the interspaced relationship of the active and return electrodes of electrode assembly allows for parallel, i.e., simultaneous, activation of the electrodes. The electric field resulting from voltage applied between the active and return electrodes is concentrated between the two, as indicated by electric field distribution 7. By adjusting the distance or gap between the active and return electrodes, the penetration depth of the electric field can be adjusted, i.e., the greater the gap, the greater the penetration depth.

Figure 3A:
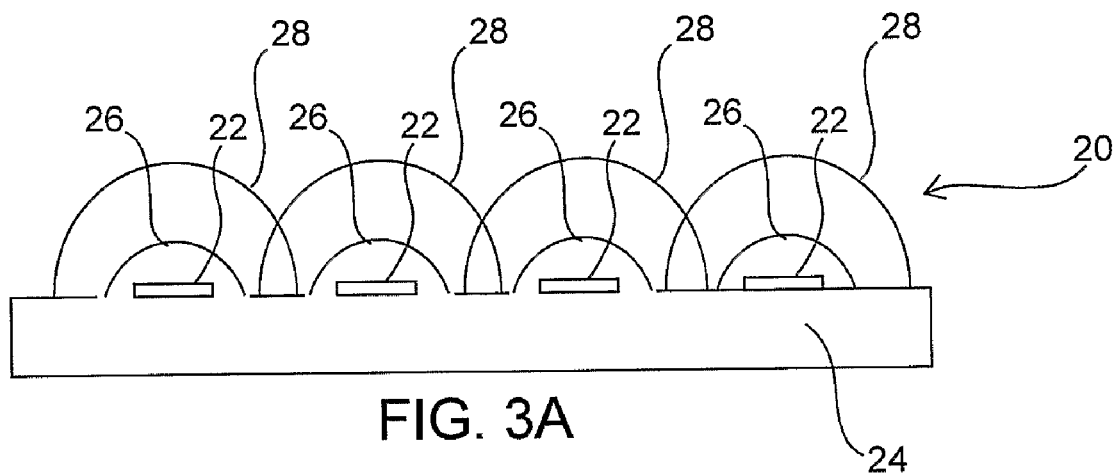
FIGS. 3A and 3B illustrate cross-sectional and top views, respectively, of another embodiment of an electrode configuration suitable for use with the present invention.
Figure 3B:
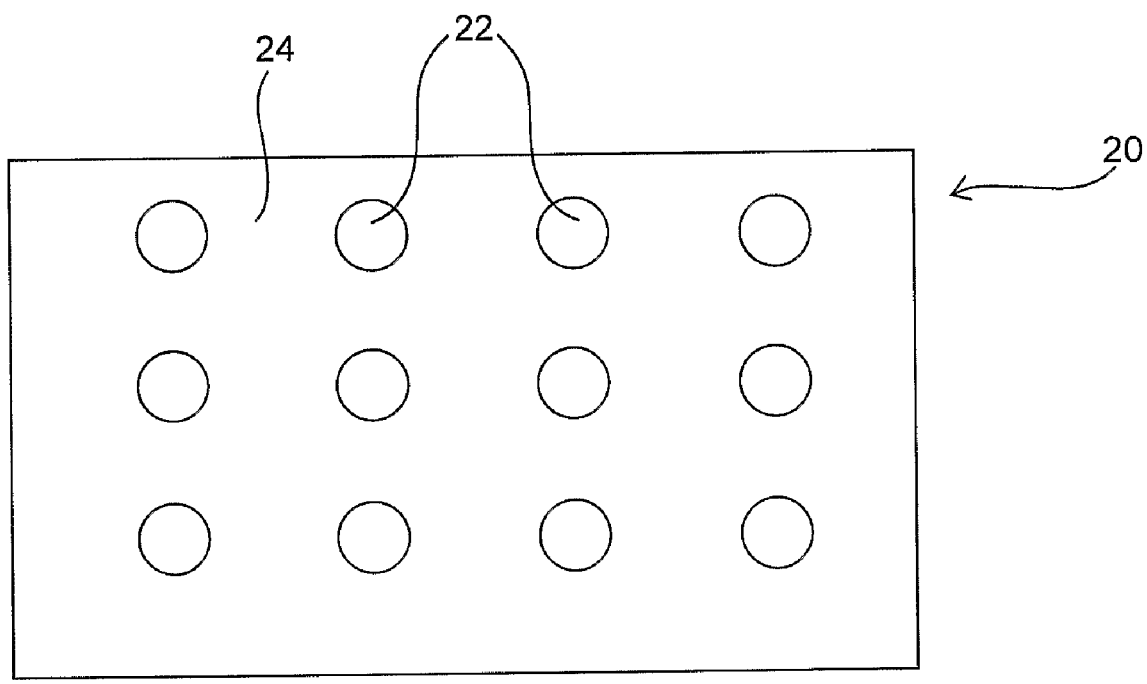
Figure 4A:
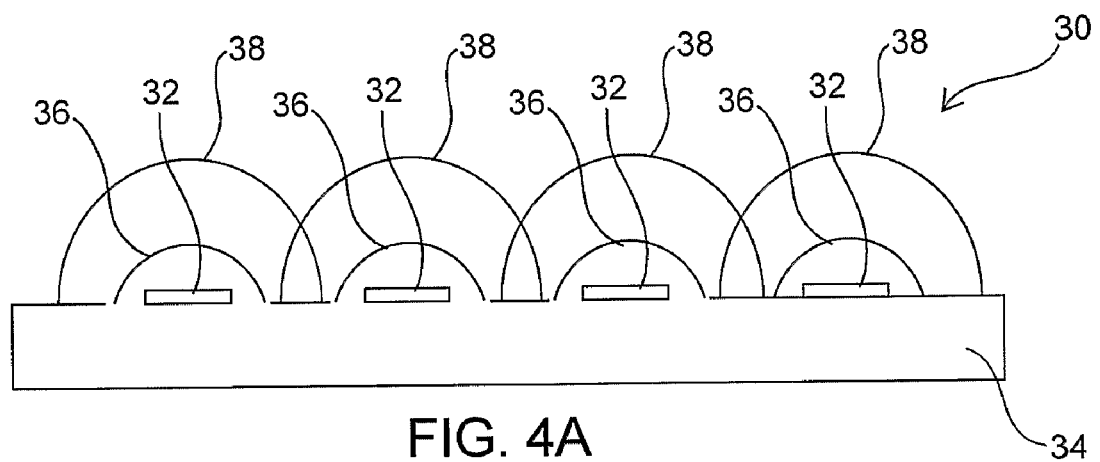
FIGS. 4A and 4B illustrate cross-sectional and top views, respectively, of another embodiment of an electrode configuration suitable for use with the present invention.
Figure 4B:
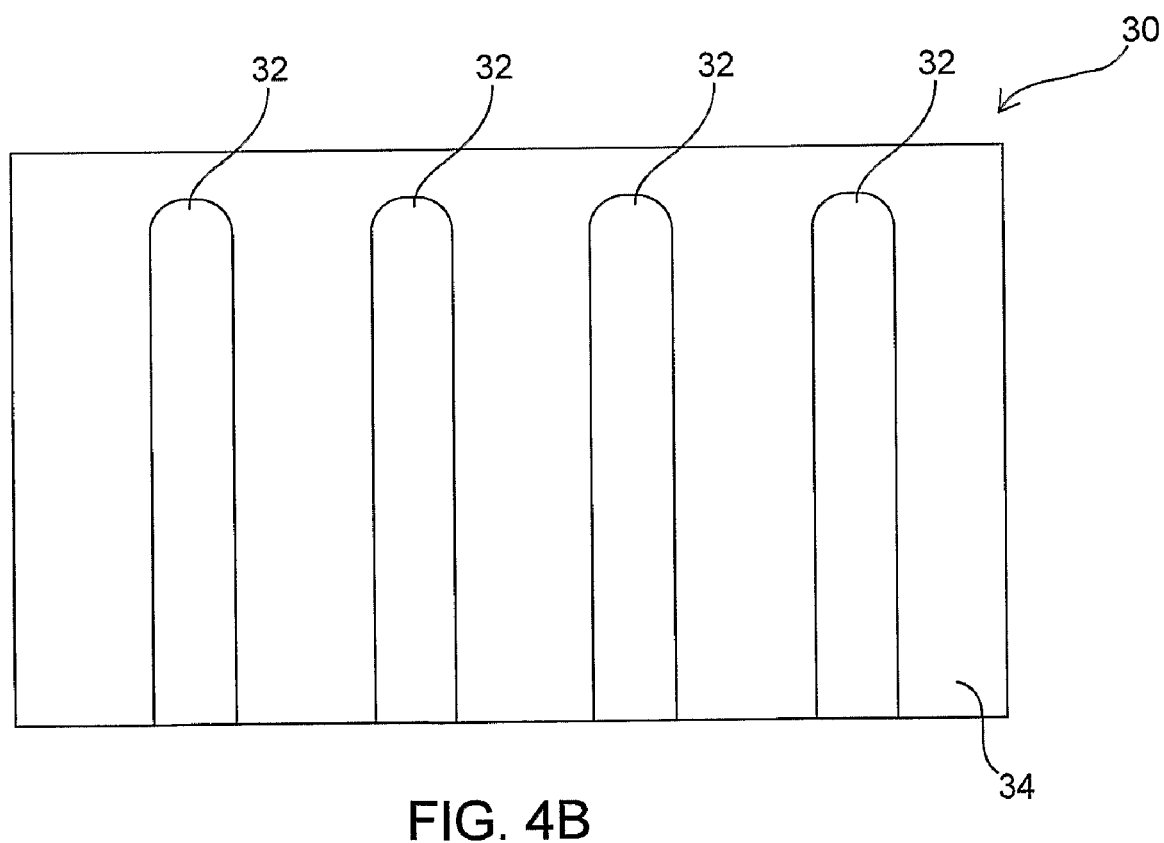
Figure 5:
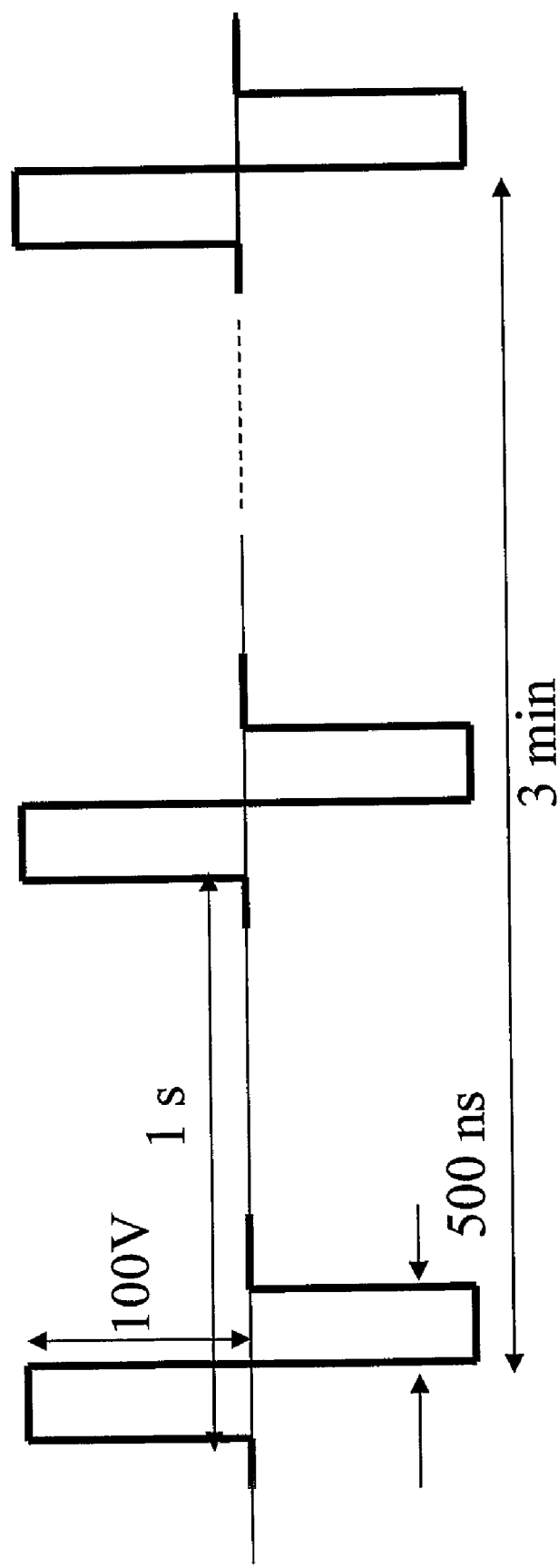
FIG. 5 is a graph an exemplary waveform of a treatment regime of the present invention.

FIGS. 3A and 3B illustrate another electrode assembly 20 having an array of active electrodes 22 mounted on an insulated substrate or support material 24. Similar to the electrode assembly of FIGS. 1A and 1B, active electrodes 22 have a dot or point configuration. FIGS. 4A and 4B illustrate another electrode assembly 30 having an array of active electrodes 32 mounted on an insulated substrate or support material 24. Similar to the electrode assembly of FIGS. 2A and 2B, active electrodes 32 are provided in the form of parallel strips of lines. Unlike the embodiments of FIGS. 1 and 2, however, the return electrode (not shown) is provided remotely, from the respective active electrode arrays, such as proximally along the probe shaft or remotely from the probe altogether With these arrangements, the active electrodes may be activated sequentially and independently of each other, where one or more active electrodes are selectively activated to control penetration depth of the field into tissue. When electrodes in the array are activated simultaneously the whole array works as a single large electrode, thus resulting in very deep penetration of the electric field—on the order of the size of the array. The sequential activation of the electrodes allows for limiting the penetration depth of electric field 26 and 36 to the width of one electrode in the array, as shown in FIGS. 3 and 4, respectively. Since the penetration depth of the electric field depends on the size and separation between the electrodes it may be selected and adjusted as necessary to obtain the desired treatment area.

The active electrodes of the electrode assemblies of the present invention may be electrically isolated from each other where each electrode is connected to a separate power source that is isolated from the other electrode terminals. The isolated power sources for each individual electrode may be separate power supply circuits, or may be a single power source which is connected to each of the electrodes through independently actuatable switches. In an alternate embodiment, the electrodes may be connected to each other at either the proximal or distal ends of the probe to form a single wire that couples to a single power source.

Various parameters of the treatment regime are selected based on the diameter(s) of the vessels to be occluded, the extent of occlusion (partial occlusion, i.e., vasoconstriction, or complete occlusion, i.e. thrombosis) and the duration or reversibility of the occlusion. Such parameters include pulse duration, burst duration where a burst includes a plurality of pulses, pulse frequency within a burst, burst frequency or repetition rate, the total treatment time where the treatment duration includes a plurality of bursts, and the electric field intensity or current density. For applications involving blood vessels, both arteries and veins, having diameters in the range from about 0.05 to about 5 mm, typical value ranges for these parameters are as follows:

| | |
|---|---|
| Pulse duration | from about 0.01 μs to about 1 ms |
| Burst duration | from about 0.2 μs to about 2 ms |
| Pulse frequency within a burst | from about 0.1 to about 10 MHz |
| Burst (or pulse) repetition rate | from about 0.01 to about 100 Hz |
| Treatment duration | from about 0.1 μs to about 1 hr |
| Electric field | from about 7 to about 35000 V/cm |
| Current density | from about 0.1 to about 500 A/cm2 |

The methods of the present invention involve electrically-induced occlusion, either partial or complete, of blood vessels in tissue. One or more active electrode(s), such as described above, are positioned in close proximity to a target region of the skin above the targeted blood vessel. The electrode assembly may be positioned on the external surface of the skin, or may be introduced through a percutaneous penetration in the outer skin surface to the targeted blood vessel(s). In the latter embodiment, the percutaneous penetration may be formed by advancing one or more needle electrodes through the outer surface of the skin to the target region of the vessel. Alternatively, an electrosurgical instrument may be introduced into the patient's vasculature and advanced transluminally to a target site. The subject methods may further be performed using traditional open surgery techniques.

Once the electrodes are positioned, a sufficient voltage, e.g. from about 1 to about 300V, is applied to the electrodes in a pulsed waveform. A resulting pulsed, monophasic or biphasic current travels through the tissue and an associated electric field develops at a desired tissue depth, typically from about 0.1 to about 5 mm from the contacted surface, where the depth is from about 0.1 to about 5 mm under the surface of the skin when treating vascular conditions of the skin, or from about 1 to about 50 mm from the contacted tissue surface when treating solid tumors.

The applied electric current produces heat energy (Joules) in the physiological medium and tissue. Electric field E applied during the time t in the medium with resistivity $\sigma$ will result in temperature rise $\Delta T = t \cdot E^2/(\rho \sigma c)$, where $\rho$ is tissue density and c is heat capacitance. For example, with $t=1$ μs and $E=20$ kV/cm only a very slight temperature change $\Delta T=1.4°$ C. occurs during the pulse, within the treated tissue region, which is far below that which would cause thermal damage. Characteristic diffusion time for electrodes of 1 mm in diameter is about 1 second, thus with pulse repetition rate of 0.1 Hz the average temperature rise will be on the order of $\Delta T_{AVE}=0.14°$ C. Thus, no thermal damage occurs with a single pulse or with a sequence of pulses.

The current waveform has a pulse duration and frequency within the ranges provided above. The resulting electric field or current density of the pulsed waveform is sufficient to induce a constriction and occlusion (thrombosis) of the blood vessel, so that blood flow through the vessel is restricted or completely interrupted. The duration of the electrical stimulation treatment will depend on the size and density of the target vascular area.

In order to further ensure that surrounding tissue and the untargeted portions of the blood vessels are not affected or damaged by the electrical stimulation, the subject methods optionally provide for the topical application of one of various protective agents or medications to areas of the patient's skin or tissue surfaces. These agents or medications fall generally within the category of calcium blockers which produce blockages in the ion channels in the cell membranes and/or the membranes of cellular organelles exposed to the agent. The calcium blockers were found to reduce or completely prevent the electrically-induced vasoconstriction. For cutaneous or subcutaneous vascular conditions, such as Port Wine Stains, the calcium blocker agent can be applied to the skin surrounding the boundaries of the vascular lesion prior to electrical stimulation. As such, the cutaneous and subcutaneous vessels in the agent-covered areas remain unaffected by the electrical stimulation. For solid tumor applications, the calcium blocker agent is applied to the skin above the location of the tumor such that only the tumor is affected by the applied electrical energy and not the skin or tissue there between. Thus, the calcium blocker agents can be used in conjunction with the electrical stimulation regimes of the present invention to chemically regulate the extent of vasoconstriction. An example of calcium blockers suitable for use with the present invention includes but is not limited to tetraethylammonium. The concentration of the agent used is usually in the range from about $1 \times 10^{-5}$ to about $1 \times 10^{-3}$ mol/L, where an exemplary concentration for tetraethylammonium is about $2.5 \times 10^{-4}$ mol/L.

EXAMPLE

The following example is put forth so as to provide those of ordinary skill in the art with an exemplary disclosure and description of how to employ the present invention, and is not intended to limit the scope of what the inventor regards as his invention nor is it intended to represent that the experiments below are all or the only experiments performed. Efforts have been made to ensure the accuracy of the data, however, some experimental errors and deviations should be accounted for.

A chorioallantoic membrane (CAM) of a chicken embryo 17 days into the incubation cycle was used for performing the experiments. Various blood vessels (three arteries and three veins) of the CAM were selected for treatment, where the vessels were of varying diameters. An electrode of 2 mm in length, 300 μm in width and 50 μm in thickness was used. Using the electrode assembly, a selected minimum threshold voltage of 100 V was applied in biphasic (having positive and negative phases in the pulse) pulses to the targeted vessels. The total biphasic pulse duration was 1 μs, the duration of each phase was 500 ns, the repetition rate was 1 Hz (1 second between the pulses) and the total treatment time was 3 minutes, at which point thrombi had formed within each of the targeted vessels. As the vessels were all approximately at the same depth beneath the exposed surface of the membrane, the threshold electric field values achieved were the same for identical applied voltages. Stasis was achieved for each vessel without thermal damage to adjacent tissue and untargeted vessels. The vessel diameter, threshold voltage and electric field, and voltage and electric field values at complete stasis are summarized in the table below.

| Vessel Type | Vessel Diameter O.D. (μm) | Threshold Voltage (V) | Threshold Electric Field (kV/cm) | Voltage at Stasis (V) | Electric Field at Stasis (kV/cm) |
|---|---|---|---|---|---|
| Artery | 75 | 80 | 7.3 | 90 | 8.2 |
| Artery | 100 | 80 | 7.3 | 170 | 15.5 |
| Artery | 225 | 80 | 7.3 | 300 | 27.4 |
| Vein | 75 | 60 | 5.5 | 90 | 8.2 |
| Vein | 150 | 60 | 5.5 | 120 | 10.9 |
| Vein | 275 | 60 | 5.5 | 250 | 22.8 |

Figure 6A:
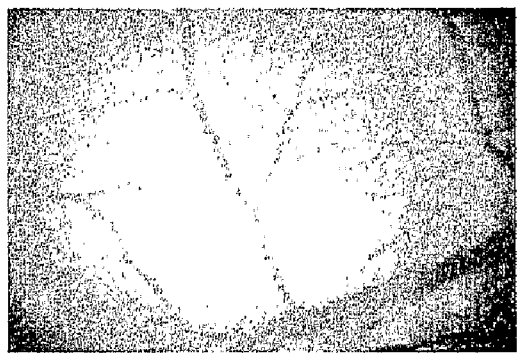
FIGS. 6A-6C illustrate videoscopic views of a chorioallantoic membrane (CAM) upon which an experiment employing the devices and methods of the present invention was conducted
Figure 7A:
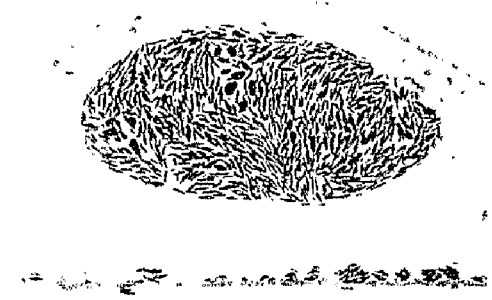
FIGS. 7A-7C illustrate histological views of a blood vessel in the CAM of FIGS. 6A-6C.
Figure 6B:
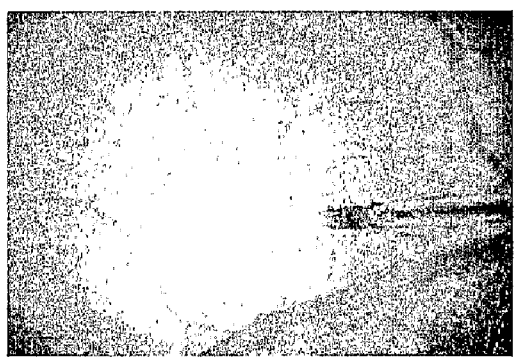
Figure 7B:
Figure 6C:
Figure 7C:

FIGS. 6A-6C are videoscopic views demonstrating the clinical appearance of the vasoconstriction and thrombosis. FIGS. 7A-7C illustrate the histological views of a CAM vessel upon which the above experiment was performed. FIGS. 6A and 7A illustrate the appearance of the targeted vessel prior to treatment according to the subject methods. FIGS. 6B and 7B illustrate the vessel as it undergoes vasoconstriction during application of the electrical stimulation protocol FIGS. 6C and 7 C illustrate the vessel after thrombosis is achieved at a targeted area of the vessel with no noticeable damage to the tissue surrounding the targeted vessel.

The present invention further includes the provision of the subject devices in the form of a kit which may include two or more of the above described electrode assemblies and various probes to be used with the catheter assemblies. The electrode assemblies may vary in size and/or geometry which may be selected for the application at hand. The kits may further include other instruments to facilitate the performance of the subject methods, including but not limited to catheter-based instruments to facilitate percutaneous delivery of the electrode assembly to a target site. The kits may further include prepackaged dosages of one or more of the above-described medications. Additionally, the kits may include instructions for using the various devices and/or medications to perform the subject methods.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of causing an occlusion of targeted vessels in a patient, the method comprising:
   contacting a tissue or skin surface of the patient with an electric probe, wherein the tissue or skin surface is proximate the targeted vessels; and
   applying electric pulses to the targeted vessels with the electric probe, the pulses each having a duration from about 0.01 µs to about 1 ms for a time period wherein the targeted vessels have achieved a desired extent of occlusion with no thermal damage to the tissue;
   wherein the desired extent of occlusion is reversible vasoconstriction of the targeted vessels.

2. The method of claim 1, wherein the electric pulses are applied at a repetition rate of about 0.01 to about 100 Hz.

3. The method of claim 1, wherein the electric pulses are applied in bursts with a pulse frequency within a burst in the range from about 0.1 to about 10 MHz.

4. The method of claim 3, wherein each burst has a duration from about 0.1 µs to about 1 ms.

5. The method of claim 4, wherein at least two bursts of pulses are applied to the targeted vessels with a repetition rate of 0.01 to 100 Hz.

6. The method of claim 1, wherein the duration of the treatment is in the range from about 0.1 microsecond to 1 hour.

7. The method of claim 1, wherein an electric field having an intensity from about 1 to about 100 KV/cm results from the applied electric pulses.

8. The method of claim 1, wherein the pulses are biphasic.

9. The method of claim 1, wherein the targeted vessels are cutaneous or subcutaneous.

10. The method of claim 1, wherein the targeted vessels support a solid tumor.

11. A method of causing an occlusion of targeted vessels in a patient, the method comprising:
    contacting a tissue or skin surface of the patient with an electric probe, wherein the tissue or skin surface is proximate the targeted vessels;
    applying electric pulses to the targeted vessels with the electric probe, the pulses each having a duration from about 0.01 µs to about 1 ms for a time period wherein the targeted vessels have achieved a desired extent of occlusion with no thermal damage to the tissue; and
    applying a calcium blocker to the tissue or skin surface prior to applying the electric pulses.

12. The method of claim 1, wherein the desired extent of occlusion is irreversible thrombosis of the targeted vessels.

13. The method of claim 1, wherein the electric probe comprises an array of electrodes.

14. The method of claim 13, wherein the electrodes are individually activated.

15. The method of claim 13, wherein the array of electrodes has a linear configuration.

16. The method of claim 13, wherein the array of electrodes has a planar configuration.

17. The method of claim 13, wherein the array of electrodes has a concentric configuration.

18. The method of claim 13, wherein the array of electrodes comprises active electrodes and the probe further comprises a return electrode positioned remotely from the array of active electrodes.

19. The method of claim 1, wherein the probe comprises at least one active electrode and a return electrode positioned remotely from the at least one active electrode, wherein the method further comprises positioning the return electrode a selected distance from said at least one active electrode.

20. The method of claim 1, further comprising providing a conductive fluid on the tissue or skin surface.

* * * * *